(12) United States Patent
Westin (10) Patent No.: US 6,782,640 B2
(45) Date of Patent: Aug. 31, 2004

(54) CUSTOM CONFORMABLE DEVICE

(76) Inventor: Craig D. Westin, 9844 S. 1300 E. Suite. 100, Sandy, UT (US) 84094

( * ) Notice: Subject to any disclaimer, the term of this patent is extended or adjusted under 35 U.S.C. 154(b) by 0 days.

(21) Appl. No.: 09/953,393

(22) Filed: Sep. 12, 2001

(65) Prior Publication Data

US 2003/0046831 A1 Mar. 13, 2003

(51) Int. Cl.[7] ............................ A34B 13/20; A34B 7/14; A61F 5/14
(52) U.S. Cl. ................................. 36/29; 36/153; 36/88
(58) Field of Search .............................. 36/29, 43, 154, 36/93, 153, 88, 35 B, 71, 160

(56) References Cited

U.S. PATENT DOCUMENTS

| | | | |
|---|---|---|---|
| 1,701,260 A | | 2/1929 | Fischer |
| 2,020,240 A | | 11/1935 | Cochran |
| 2,177,116 A | | 10/1939 | Persichino |
| 3,121,430 A | | 2/1964 | O'Reilly |
| 3,253,591 A | | 5/1966 | Scholl |
| 4,217,705 A | * | 8/1980 | Donzis ........................... 36/29 |
| 4,845,861 A | * | 7/1989 | Moumdjian .................... 36/29 |
| 4,991,317 A | | 2/1991 | Lakic |
| 5,199,191 A | | 4/1993 | Moumdjian |
| 5,203,793 A | | 4/1993 | Lyden |
| 5,383,290 A | | 1/1995 | Grim |
| 5,469,592 A | * | 11/1995 | Johnson ......................... 36/43 |
| 5,617,650 A | * | 4/1997 | Grim ............................. 36/88 |
| 5,741,568 A | * | 4/1998 | Rudy ............................ 36/29 |
| 5,878,510 A | | 3/1999 | Schoesler |
| 5,918,383 A | * | 7/1999 | Chee .......................... 36/35 B |
| 5,996,253 A | * | 12/1999 | Spector ......................... 36/29 |
| 6,425,195 B1 | * | 7/2002 | Donzis .......................... 36/88 |

FOREIGN PATENT DOCUMENTS

| WO | WO91/06229 A1 | * | 5/1991 | ........... A43B/2/14 |
|---|---|---|---|---|
| WO | WO95/00047 A1 | * | 1/1995 | ........... A43B/17/03 |

* cited by examiner

Primary Examiner—Anthony Stashick
(74) Attorney, Agent, or Firm—McGuireWoods LLP (57) ABSTRACT

A custom conformable device that supports and cushions a user's anatomical part, such the foot. The device is self-inflating, conforms to the shape of the user's foot, utilizes an inflatable bladder with a valve, and contains an expandable material such as an open cell foam. When the valve is open the expandable material expands, causing the bladder to inflate and to conform to the shape of the user's anatomical part. Once the desired shape is achieved, the valve is closed, sealing the bladder. Once the bladder is sealed, the expandable material retains the shape of the user's anatomical part. The user may open the valve to adjust the level of support provided by the device by allowing more fluid to enter the bladder, or by forcing fluid to exit the bladder.

20 Claims, 4 Drawing Sheets

CUSTOM CONFORMABLE DEVICE

BACKGROUND OF THE INVENTION

1. The Field of the Invention

The present invention relates to orthotics and custom conformable devices, including custom fitting orthotics.

2. The Relevant Technology

Orthotics is the science of treating anatomical disorders, such as joint, bone, or muscle disorders, with anatomical supports, such as braces, inserts, and cushions. Anatomical supports have been commonly used both to increase comfort and to aid in medical treatments. For instance, arch supports have been used for many years for both added foot comfort when wearing shoes, and for treatment of foot and knee problems. Arch supports fall into one of two common categories: (1) inserts that increase padding or cushion; and (2) corrective devices, commonly referred to as orthotics, that correct foot position to relieve stress on the foot, knee or leg. Orthotics are commonly used to support feet with normal alignment, and to correct feet that have excessive pronation.

Pronation is the inward rotation of the middle part of the foot, and is commonly associated with a low arch. One function of orthotics is to prevent the natural pronation of the normal foot during walking. Three separate arches are described that support the weight of the body. These arches are not rigid and provide flexibility and leverage for walking. With normal walking, the foot lands in a supinated or high arch position at heel strike. As weight is accepted by the foot during walking, the arch flattens and the foot pronates until it is at maximum pronation and maximum load, approximately 25% of the way into the stance. The foot then resupinates until push off, when all weight is removed from the foot. One function of orthotics is to shorten the period of time in pronation during stance phase of gait to reduce stress on the tendons of the foot and knee. Orthotics should exert a gentle, consistent pressure to bring the foot into proper alignment. Correction of hyper pronation, or "flat feet," is another function of orthotics. The relief of excessive pronation can relieve other conditions such as shin splints or kneecap problems.

Two categories of orthotics are commonly available: (1) ready-made orthotics; and (2) custom molded or custom fit orthotics. Ready-made orthotics typically come in standard sizes and are relatively inexpensive. One problem with ready-made orthotics is that they often fit poorly or are uncomfortable because they do not accommodate the unique shape and size of each patient's foot. Custom molded orthotics are intended to solve this problem. Custom fit orthotics are custom made to fit a particular foot size and shape, and thus they ought to fit comfortably on each patient. One problem with custom molded orthotics is that they often require the services of an expert to custom fit the orthotic, and they can be cost prohibitive due to the time and expertise required to custom make each orthotic.

Attempts have been made to provide custom molded orthotics that are custom fit by the user and less cost prohibitive than traditional custom molded orthotics. One such attempt utilizes a variety of chemicals in a liquid state placed inside an insole. First, the user initiates a chemical reaction in the chemicals within the insole. Next, the user places the insole inside a shoe, and wears the shoe as normally worn. The weight of the user on the insole molds the liquid chemicals inside insole to conform to the shape of the user's foot. The chemical reaction occurring inside the insole causes the chemicals to transform from a liquid state to a solid state, resulting in a solid orthotic in the shape of the user's foot. Although such a custom molded orthotic is less cost prohibitive and does not require an expert to mold the orthotic, the problem with such molded orthotics is that the user cannot adjust the level of support of the orthotic. The amount of chemicals in the insole determines the size and level of support of the orthotic, thus the orthotic will not give the desired level of support unless it initially contains the correct amount of liquid chemicals. The desired level of support may not be known by the user until the chemicals in the orthotic have set and the user feels the level of support given by the orthotic. However, once the chemicals have set, the level of support cannot be adjusted. Thus, the orthotic will conform to the user's foot but often does not provide the level of support desired.

Another attempt to provide custom fit orthotics that are custom fit by the user and less cost prohibitive than traditional custom molded orthotics utilizes a bladder filled with air. An air bladder is placed inside an insole, which is placed inside the user's shoe. Some embodiments require the user to use a pump to inflate the bladder before the shoe is placed on the user's foot. Other embodiments incorporate a pump inside the insole or shoe. The weight of the user works the pump, which inflates the bladder as the user walks while wearing the shoe. The inflated bladder is intended to conform to the shape of the user's foot as weight is placed on the user's foot.

Although some of such conventional custom fit orthotics allow the user to adjust the level of support of the orthotic, these custom fit orthotics may be complex to manufacture, involving complex pumps to inflate the bladder. The complex design and numerous parts required to inflate the bladder can be cost prohibitive. Further, the inflated bladder does not retain the shape of the user's foot when weight is removed from the foot.

The bladder is filled in these conventional devices with a fluid, in this case a gas, that freely shifts and flows inside the bladder as the weight on the user's foot shifts, thus causing the inflated bladder to change shape. Such a shifting of shape during different stages of walking may result in undesired changing levels of support.

What is needed is a custom fit support that conforms to shape of the user's anatomy, retains the shape of the user's anatomy, is efficient to manufacture, is relatively inexpensive, and has an adjustable level of support.

BRIEF SUMMARY OF THE INVENTION

It is, therefore, an object of the present invention to provide a custom conformable device that conforms to the shape of the user's anatomy.

It is another object of the present invention to provide a custom conformable device that is inexpensive and efficient to manufacture.

It is another object of the present invention to provide a custom conformable device that may be custom fit by the user.

It is another object of the present invention to provide a custom conformable device that has a level of support that can be adjusted by the user.

It is another object of the present invention to provide a custom conformable device that retains the shape of the user's anatomy when weight is removed from the support.

It is another object of the present invention to provide a custom conformable device that conforms to the shape of the user's foot.

It is still another object of the present invention to provide a custom conformable device that gently compresses blood vessels in an anatomical part of the user, such as the arch of the foot, to promote circulation.

To achieve the foregoing objects, and in accordance with the invention as embodied and broadly described herein, a custom conformable device that conforms to the shape of the user's anatomy is provided. The custom conformable device comprises a bladder containing some expandable material such as open cell foam, and a valve. When the valve is opened to admit a fluid flow into the bladder that contains compressed expandable material, for example when the valve is opened to the atmosphere, the expanding expandable material causes the bladder to self-inflate, eliminating the need for complex pumps or parts to inflate the bladder; thereby making the support efficient and inexpensive to manufacture. The custom conformable device conforms to the shape of the user's anatomy as it inflates. Once the bladder has inflated to a desired level of support, the valve is closed, sealing the bladder. The expandable material, such as open cell foam, retains the shape of the user's anatomy once the bladder is sealed. Finally, the user may open the valve to further inflate or deflate the bladder, adjusting the level of support.

The bladder has a valve that admits or releases a fluid from the bladder. This fluid is air in a preferred embodiment. Before using the custom conformable device, the valve is opened and the bladder is compressed to compress the expandable material and to deflate the bladder. The valve is then closed so that the bladder remains deflated and the expandable material remains compressed. The custom conformable device is then placed in position between the anatomy of the user and some other object, such as the back of a seat, the interior of a shoe, the floor, the interior of a brace, such as a lower extremity brace, etc. Before placing weight on the custom conformable device, the user opens the valve of the bladder, allowing the bladder to self-inflate. The expandable material inside the bladder expands, drawing air into the bladder, and causing the bladder to inflate. As the bladder inflates, it conforms to the shape of the user's anatomy. Once the bladder has inflated to the desired level, the user closes the valve, sealing the air inside the bladder. The expandable material incrementally expands after the valve is closed, thus creating a rarefaction inside the bladder with respect to the surrounding environment. This rarefaction contributes to the retention by an embodiment of the custom conformable device of this invention of the shape of the body part to which it is applied. The custom conformable device is now ready for use by the user.

The inflated bladder supports and cushions the anatomy of the user. The expandable material such as open cell foam retains the shape of the support when weight is removed from the custom conformable device. Thus the shape and level of support of the custom conformable device is constant during use by the user. The user may also open the valve at any time to either allow more fluid to enter the bladder, increasing the level of support, or to expel fluid from the bladder, decreasing the level of support.

Embodiments of custom conformable devices according to the present invention become custom fit when they conform to the user's anatomy as described herein. Embodiments of custom conformable devices according to the present invention provide various forms of custom fit support to the user's anatomy.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

The present invention relates to custom conformable devices with a self-inflating bladder that conforms to the shape of a user's anatomy. The present invention may be used to make a variety of devices used to support a part of a user's anatomy against another surface. By way of example and not limitation, the present invention may be used to make a plurality of embodiments of custom conformable devices, such as a pillow-like head support to be used while either sitting in a seat or lying down; a back support to be placed behind the back of a user sitting in a seat; an arch support to be placed inside the shoe of a user; a support for a patient undergoing a surgical procedure; and a brace to be applied to an extremity.

Figure 1:
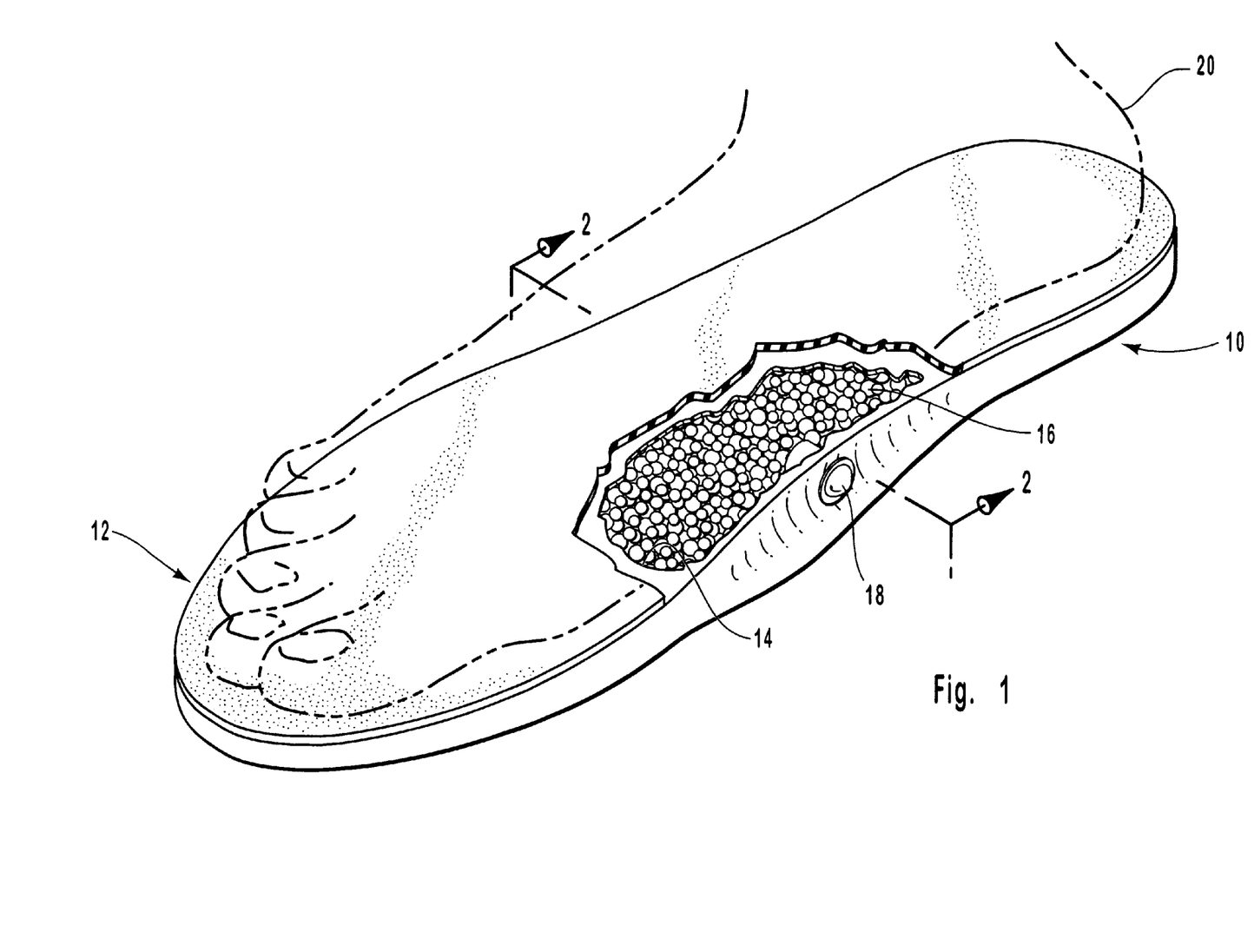
FIG. 1 illustrates a top view of one embodiment of a custom conformable device for use as a custom fit orthotic.

Illustrated in FIG. 1 is one embodiment of a custom conformable device 10 incorporating features of the present invention. The custom conformable device 10 comprises an insole 12 and an inflatable bladder 14. Insole 12 is shaped such that when placed in a shoe, insole 12 substantially retains the position of inflatable bladder 14 under the arch of the user's foot as shown by ghost outline 20 of the user's foot. The embodiments shown in the accompanying drawings illustrate by way of example a valve, such as valve 18, that opens to the atmosphere and regulates the passage of air flow.

Gas flow is a preferred fluid flow, and air flow is a more preferred fluid flow it in embodiments of this invention. This fluid flow can be embodied by other fluids, including gases and liquids, taken into and expelled from the bladder in other embodiments of this invention. Air is expelled from the interior of bladder 14 by external compression of the bladder.

The illustrative embodiment shown in FIG. 1 extends throughout the entire bottom surface of foot 20. Other embodiments of the present invention extend only throughout part of the bottom surface of the foot, such as, for example, the surface below the arch, and still other embodiments extend throughout part of some other region of the foot, such as the side and the top.

Inflatable bladder 14 has a valve 18 and contains expandable material 16. Valve 18 is located on bladder 14 such that valve 18 is easily accessible by the user of custom conformable device 10. Valve 18 is preferably located on the side of bladder 14 below the arch of the user's foot such that valve 18 does not cause discomfort to the user's foot. As illustrated in the figures, valve 18 permits to control the flow of air into and from the interior of inflatable bladder 14, and is preferably a finger-activated valve.

Embodiments of valves according to the present invention include finger-activated valves, button valves, umbrella valves, duck-bill valves, central stem valves such as Schraeder-type valves, and generally valves that perform like the valves typically found in bicycle and car tires.

Means for controlling passage of gas into and from the bladder according to the present invention include finger-activated valves, button valves, umbrella valves, duck-bill valves, central stem valves such as Schraeder-type valves, and generally valves that are actuated by external pressure and then perform like the valves typically found in bicycle and car tires, such that the fluid flow into the bladder and through the valve is drawn by expandable material within the bladder that expands from a compressed state to a more expanded state.

As described herein, embodiments of valves and means for controlling passage of a gas into and from the bladder according to the present invention are preferably configured in a such a way that they can be repeatedly activated, so that the operations of allowing gas to flow into and/or to flow from the interior of the bladder can be repeated many times at the user's choice. This characteristic is referred to herein as "multiple activation". To facilitate multiple activation, embodiments of valves and means for controlling passage of a gas into and from the bladder according to this invention are preferably partially exposed, so that they can be reached easily.

In addition to embodiments with one valve or with one means for controlling passage of a gas into and from the bladder, this invention envisages embodiments with a plurality of valves or with a plurality of means for controlling the passage of gas into and from the bladder. For example, embodiments according to the present invention can be provided with two valves. One of the valves in these embodiments can be chosen for quick deflation, whereas the other valve can be a low fluid flow valve for a more controlled regulation of the degree of inflation of the custom conformable device. Analogous considerations apply to embodiments with, for example, two means for controlling passage of a gas into and from the bladder.

Expandable material 16 within bladder 14 is compressible, it is capable of assuming a compressed and an expanded form, and is preferably an open cell foam. At least part of expandable material 16 is embodied by particulate material in some embodiments. The particulate material is loose and contained within the bladder in some of the embodiments with particulate material. Expandable material 16 fills the interior of bladder 14 in preferred embodiments of the present invention. Expandable material 16 partially fills the interior of bladder 14 in other embodiments of the present invention.

The terms "expandable material" are used herein as the concise form for expandable material medium. Expandable material comprises an expandable material medium that is capable of expanding and contracting throughout at least a substantial portion of such material medium, and such that fluid is drawn into the medium when expanding. This feature distinguishes expandable material as used herein from a container such as a hollow shell, balloon or empty vessel that could expand upon inflation and contract upon deflation, but that would not experience expansion and contraction throughout at least a substantial portion thereof because such shell, balloon or vessel provides no medium therein. The expansion and contraction is experienced in these hollow containers only by the container walls, as opposed to the expansion and contraction of a material medium throughout the expandable material of the present invention. Furthermore, these hollow containers cannot retain a particular shape when they are partially or completely inflated.

The expandable material according to the present invention comprises solid material throughout the expandable material itself. This material provides a supportive element that does not shift throughout the interior of a container when the expandable material is contained therein and pressure externally applied to such container changes. A foam is an illustrative example of an expandable material, the foam providing itself a material medium that has the properties referred to hereinabove.

The expandable material according to the present invention provides itself a material medium that does not shift as a fluid when it is within a container subjected to changing external pressure. The property of "not shifting as a fluid" as used herein indicates that the substance to which it is applied does not flow when it is within a container that is subjected to changing external pressure. Furthermore, the expandable material according to the present invention provides a material medium that draws fluid throughout at least a portion of such material medium itself. These properties distinguish the expandable material of the present invention from an hollow container with only fluid therein, where the fluid can shift within the container as external pressure changes. These properties also distinguish the expandable material of the present invention from a container that only has in its interior fluid in combination with a material that does not absorb fluid itself.

Before use, valve 18 is opened and inflatable bladder 14 and expandable material 16 are compressed, with inflatable bladder 14 substantially deflated so that conformable device 10 is substantially flat. Valve 18 is then closed and the external compressive pressure is released or at least decreased, thus creating a degree of rarefaction inside inflatable bladder 14 when expandable material 16 tends to expand upon the release or diminution of the external pressure. This degree of rarefaction in the inflated device with respect to the surrounding environment is concisely referred to for simplicity as a vacuum. With valve 18 closed, expandable material 16 is prevented from expanding to a large extent.

Custom conformable device 10 thus retains a substantially flat form until valve 18 is opened and expandable material 16 is allowed to expand, thus drawing air into and inflating inflatable bladder 14. Valve 18 is closed when inflatable bladder has inflated to a desired extent, and expandable material 16 further expands to some extent, which is termed as undergoing an incremental expansion, with valve 18 closed. This incremental expansion creates a vacuum within the inflated bladder that contributes to the retention by the custom conformable device of the shape of the body part to which it is applied. Filled and hollow containers that provide cushioning effect upon their complete inflation are devoid of this property.

Inflatable bladder 14 provides an example of a self-inflating bladder in an embodiment of a self-inflating custom conformable device according to the present invention. Reference to FIG. 1 in the description of the inflation of a custom conformable device is merely illustrative, and such mechanism applies to preferred embodiments of custom conformable devices according to this invention, without limitation to the structural features shown in FIG. 1.

Figure 2:
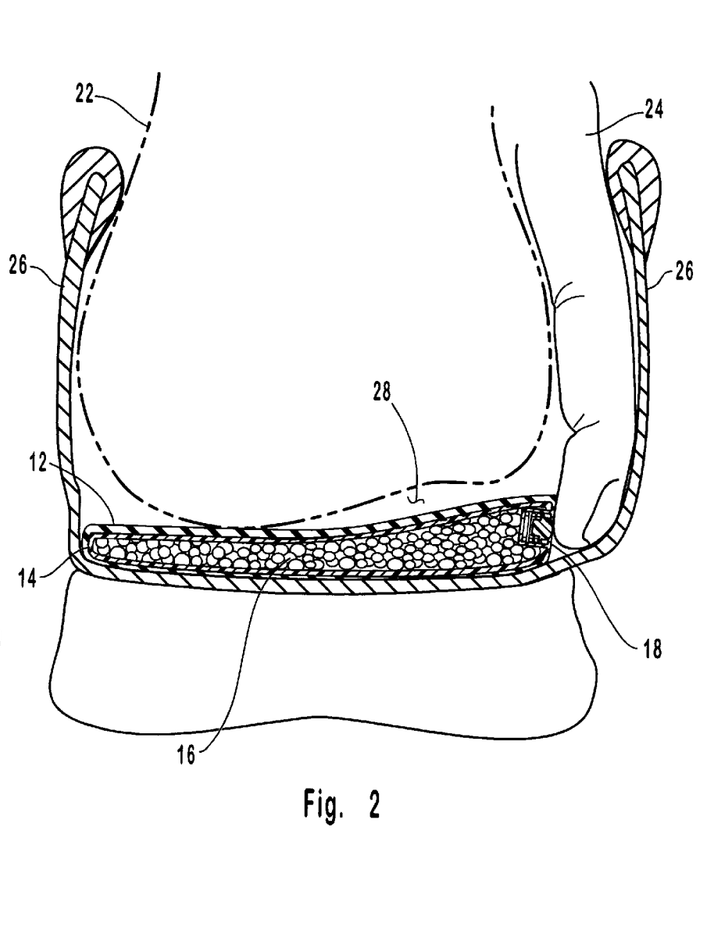
FIG. 2 illustrates a cross-sectional view of an embodiment of a custom conformable device placed inside a shoe of a user, the device being in a deflated state.

As illustrated in FIG. 2 that shows the cross-sectional view 2—2 indicated in FIG. 1, custom conformable device 10 is placed into shoe 26, and shoe 26 is placed on foot 22 of a user. Custom conformable device 10 is preferably placed into shoe 26 in a substantially deflated and flat form. If custom conformable device 10 is inflated when it is placed into shoe 26, the user can deflate it by opening valve 18 and pressing with foot 22 against the ground.

The natural shape of foot 22 creates a space 28 between custom conformable device 10 and foot 22. Inflatable bladder 14 is configured such that when fully inflated, inflatable bladder 14 fills space 28 in the unweighted foot. Before weight is placed on foot 22, for example when the user is sitting or shifting all or at least a significant portion of the body weight to the other foot, a finger, illustrated by finger 24, is then inserted into shoe 26 to open valve 18. This operation allows the flow of air into bladder 14 as expandable material 16 expands. This flow of air is controlled by the operation of valve 18 by the user.

Some embodiments of the present invention are configured so that an extension member coupled to a valve such as valve 18 is used to open and close the valve without having to insert a finger through the space between the foot and the shoe all the way down to reach the valve itself By way of illustration but not as a limitation, an example of such extension member is the extension provided in various duck-bill valves to actuate the valve and regulate the fluid flow therethrough.

Expandable material 16 expands when valve 18 is open, drawing air into inflatable bladder 16. As inflatable bladder 16 inflates, inflatable bladder 16 fills space 28 and conforms to the shape of foot 22.

Figure 3:
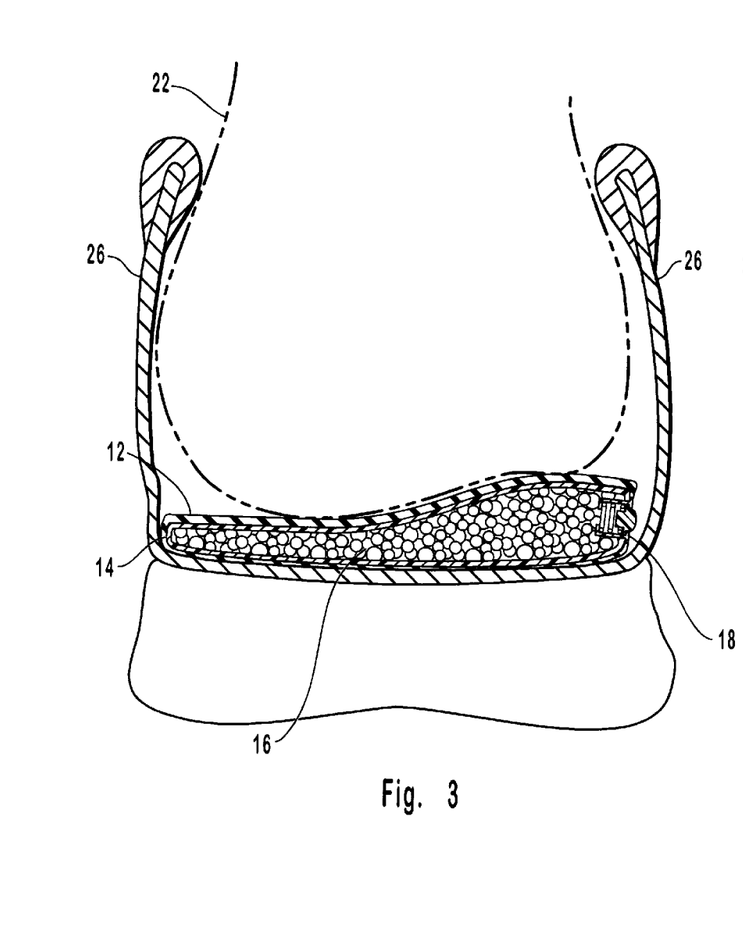
FIG. 3 illustrates a cross-sectional view of an embodiment of a custom conformable device placed inside a shoe of the user, the device being in an inflated state.

The cross sections shown in FIGS. 2–3 can also represent cross sections of embodiments of custom conformable devices that extend only through part of the bottom surface of the foot or some other body part.

FIG. 3 illustrates an inflated custom expandable material. Inflatable bladder 14 and expandable material 16 fill space 28 and conform to the shape of foot 22. When inflatable bladder 14 has inflated to the desired level, the user closes valve 18. Once valve 18 is closed, the user may apply weight to foot 22 and wear the shoe normally. Inflated bladder 14 supports and cushions foot 22 as the user walks or runs. Expandable material 16 retains inflated bladder 14 in conformation to the shape of foot 22 regardless of how the weight of the user shifts on foot 22 during walking or movement.

Depending on the composition of specific embodiments of the expandable material, changes in pressure applied to the expandable material while in use will cause slight variations in its shape according to its firmness and springiness. Terms such as "substantially retains the shape of the user's anatomical part" are used herein to refer to these variations. Similarly, the adverb "substantially" is applied herein to qualify terms related to the bladder because of variations in the anatomical part to which it is applied and variations derived from the physical properties of the bladder material itself.

Figure 4:
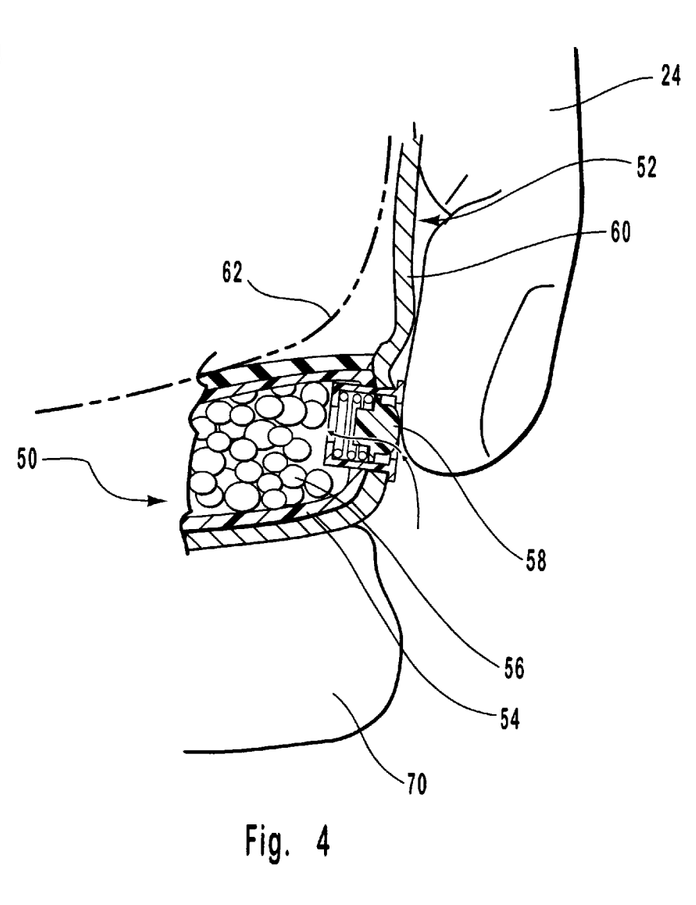
FIGS. 4–5 illustrate another embodiment of a custom conformable device as an integral part of a shoe, where a valve is opened as shown in FIG. 4 to inflate the device which is depicted in FIG. 5 in an inflated state.

FIG. 4 illustrates another embodiment of a custom conformable device as an integral part of a shoe. In this embodiment, custom conformable device 50 is manufactured as an integral part of shoe 52, and resides above sole 70 of shoe 52. Custom conformable device 50 comprises an inflatable bladder 54, has a valve 58, and is filled with expandable material 56. Valve 58 extends through, for example, wall 60 of shoe 52 such that the valve may be opened and closed from the outside of shoe 52.

Before use of custom conformable device 50, shoe 52 is placed on foot 62 of a user. Weight is placed on foot 62, for example by shifting weight to foot 62 or by simply standing, and valve 58 is opened. The weight placed on foot 62 substantially deflates inflatable bladder 54 and substantially compresses expandable material 56. The user then closes valve 58 and removes the weight from foot 62, for example by shifting body weight to the other foot or by sitting down. The user now uses the custom conformable device in the same way as the embodiment described in FIGS. 1–3.

Figure 5:
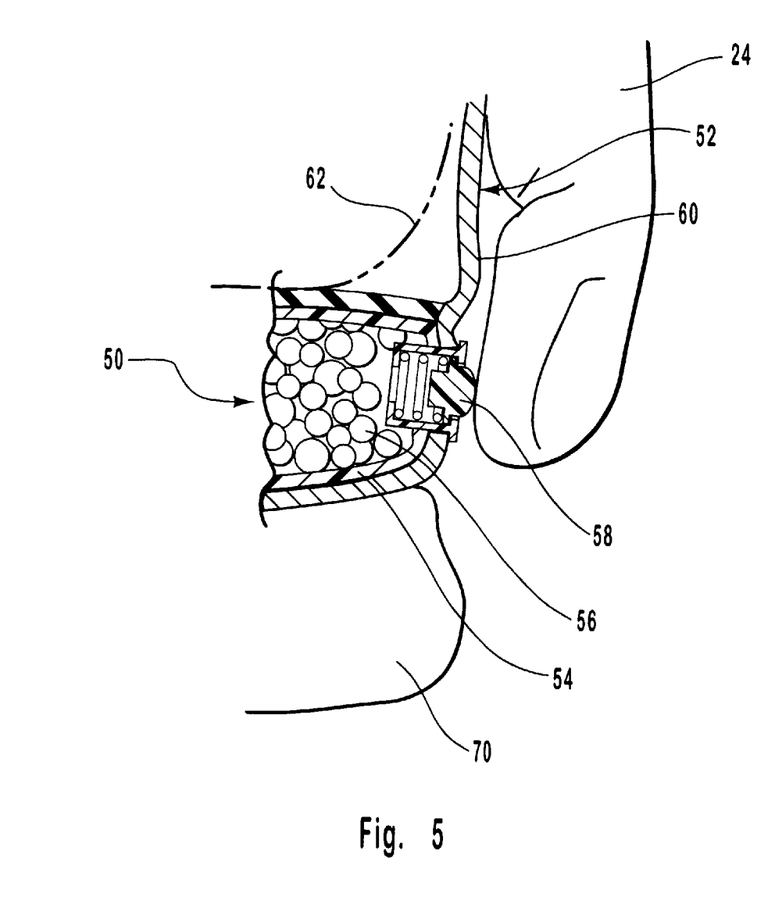

The user opens valve 58, allowing expandable material 56 to expand, inflating inflatable bladder 54. Inflatable bladder 54 and expandable material 56 fill space 68 and conform to foot 62. Once inflatable bladder 54 has inflated to the desired level, valve 58 is closed, sealing the air inside inflatable bladder 54. The user then wears the shoe normally, and can adjust the level of support of custom conformable device 50 at any time by opening valve 58 to admit or to expel air.

Inflation and deflation operations such as those described hereinabove can be performed as many times as desired by the user of embodiments of the present invention. Expandable material 56 retains the shape of custom conformable device 50 regardless of the shifting weight on foot 62 during walking or other movement by the user.

Bladder 54 extends in some embodiments of the present invention throughout the entire shoe sole, whereas in other embodiments it extends throughout a partial area of the shoe sole, for example, under the foot arch only, in which case the bladder perimeter has a shape such as an approximately trapezoidal shape or a curved shape. In some embodiments of the present invention, bladder 54 is on the shoe sole, whereas in other embodiments it is formed within the shoe sole itself.

The term "shoe" is used herein to describe a foot-borne item on at least a part of which the foot rests, and such that this item moves together with the foot when walking or displacing the foot. This term as used herein comprises, but is not limited to, different types of shoes, such as athletic shoes, dress shoes, slippers, boots, casual shoes, sandals, shoes that are configured for use in conjunction with another device, such as skates and skis, and orthopedic shoes.

FIGS. 2–4 illustrate by way of example an embodiment of the present invention inserted below the bottom of a foot. Embodiments of the present invention are also configured for their insertion between some other anatomical region and an item that allows for the implementation of operations such as the following: inflation and deflation of the bladder, compression and expansion of the expandable material by controlled application of external pressure, and fluid flow regulation from and into the interior of the bladder. For example, embodiments of custom conformable devices according to this invention can be placed between an interior area of a shoe, such as a ski boot, a hiking boot and a running shoe, and a specific region of the foot that is to be cushioned and/or supported when the user wears such ski boot, hiking boot or running shoe.

Embodiments of expandable material according to the present invention include open cell foam, open cell foamed polyester, open cell foamed polyether, open cell polyurethane, open cell glassy carbon foam, combinations of open cell foam and a material, such as semi-closed cell and closed cell foam, for added resilience. Open cell foam, such as medium density polyurethane open cell foam, is a preferred embodiment of expandable material. Further embodiments of expandable material according to the present invention comprise a composite of a foam and open cell metal foams, which have the additional advantages of a resilient component and a heat-dissipating component, and combinations of the foregoing embodiments of expandable material. Various embodiments of expandable material according to the present invention include materials such as those described herein, including these materials in mechanically shaped form, in particulate form, thermo-formed, and combinations thereof.

Means for inflating a bladder according to the present invention include open cell foam, open cell foamed polyester, open cell foamed polyether, open cell polyurethane, open cell glassy carbon foam, combinations of open cell foam and a material, such as semi-closed cell and closed cell foam, for added resiliency, and combinations of the foregoing embodiments of means for self-inflating a bladder. Open cell foam, such as medium density polyurethane open cell foam, is a preferred embodiment of means for inflating a bladder.

Further embodiments of means for inflating a bladder according to the present invention comprise a composite of a foam and open cell metal foams, which have the additional advantages of a resilient component and a heat-dissipating component, combinations of the foregoing embodiments of means for inflating a bladder. Additional embodiments of means for inflating a bladder according to the present invention generally include open-cell-comprising materials that perform with respect to compression and expansion in a manner similar to the foregoing examples of means for inflating a bladder.

Embodiments of means for inflating a bladder according to the present invention provide a material medium that does not shift as a fluid when it is within a container subjected to changing external pressure. Furthermore, embodiments of means for inflating a bladder according to the present invention provide a material medium that draws fluid throughout at least a portion of such material medium itself.

The embodiments of means for inflating a bladder according to the present invention include materials such as those described herein, including these materials in mechanically shaped form, in particulate form, thermo-formed, and combinations thereof.

Means for substantially retaining the shape of a bladder according to the present invention include open cell foam, open cell foamed polyester, open cell foamed polyether, open cell polyurethane, open cell glassy carbon foam, combinations of open cell foam and a material, such as semi-closed cell and closed cell foam, for added resiliency, and combinations of the foregoing embodiments of means for substantially retaining the shape of a bladder. Open cell foam, such as medium density polyurethane open cell foam, is a preferred embodiment of means for substantially retaining the shape of a bladder.

Further embodiments of means for substantially retaining the shape of a bladder according to the present invention comprise a composite of a foam and open cell metal foams, which have the additional advantages of a resilient component and a heat-dissipating component, combinations of the foregoing embodiments of means for self-inflating a bladder. Additional embodiments of means for substantially retaining the shape of a bladder according to the present invention generally include open-cell-comprising materials that perform with respect to shape retention in a manner similar to the foregoing examples of means for substantially retaining the shape of a bladder.

Embodiments of means for substantially retaining the shape of a bladder according to the present invention provide a material medium that does not shift as a fluid when it is within a container subjected to changing external pressure. Furthermore, embodiments of means for substantially retaining the shape of a bladder according to the present invention provide a material medium that draws fluid throughout at least a portion of such material medium itself.

The embodiments of means for substantially retaining the shape of a bladder according to the present invention include materials such as those described herein, including these materials in mechanically shaped form, in particulate form, thermoformed, and combinations thereof.

The means for substantially retaining the shape of a bladder and the means for inflating a bladder are embodied by the same material in some embodiments of the present invention, whereas they are embodied by different materials in other embodiments of the present invention.

Different embodiments of the bladder material according to the present invention comprise materials such as vinyl; polyurethane; materials, including composites, with flexible fabrics such as neoprene coating material; elastic film materials; composites with flexible fabrics of natural and manufactured fibers; and combinations of such materials.

The closed cell materials in structures of composites with closed cell materials comprised in embodiments of the present invention resemble a cellulose kitchen sponge, with all or at least most of the cells separated from one another by walls. The structures of open cell materials comprised in embodiments of the present invention resemble a loofah sponge, with holes of varying size. The preferred hole size range of open cell materials being such that the expandable material effectively draws fluid into its interior and thus into the interior of its surrounding bladder through the open valve when the expandable material expands from a compressed state.

The expandable material is loose and contained within the bladder in some embodiments of the present invention. The bladder is embodied by a shell that is integrally formed around the outer surface of the expandable material in other embodiments of the present invention. In other embodiments of the present invention, a supportive core of open cell foam is bonded between two layers of closed cell foam that enclose the open cell foam core in fluid-leak-proof containment and the bonded material has a valve to control fluid flow therethrough.

The expandable material or the bladder comprises a plurality of laminated materials in other embodiments of the present invention. The expandable material and the bladder comprise a plurality of laminated materials in still other embodiments of the present invention.

Some embodiments of the present invention include an insole that substantially retains the bladder in a selected position, such as below the arch of the foot of the user when the insole is placed in a shoe and worn by the user. The insole is preferably attached to the bladder in these embodiments.

Figure 6:
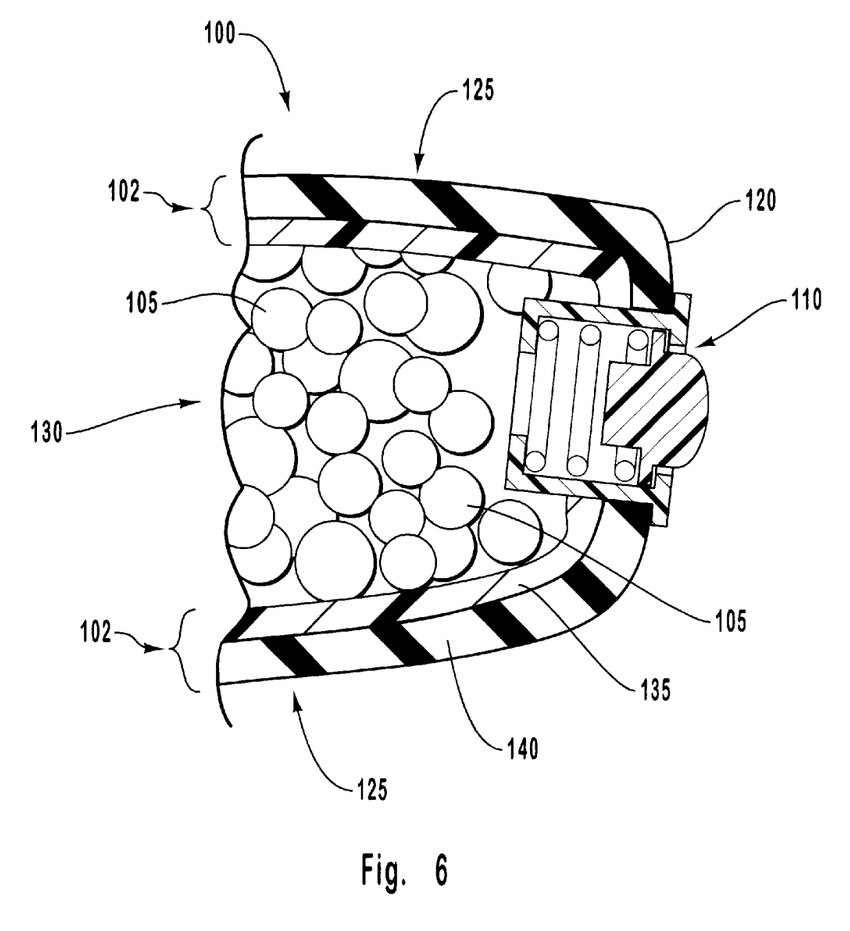
FIG. 6 illustrates a portion of a cross-sectional view of an embodiment of a multi-layered custom conformable device.

FIG. 6 illustrates a cross-sectional view of a portion of an embodiment 100 of a custom conformable device that can be embodied by devices such as shoe inserts, pillows, arm rests, back rests, and orthopedic braces.

Illustrative shoe inserts as custom conformable devices according to the present invention are embodied by shoe inserts that extend only to part of the bottom foot surface, shoe inserts that extend to the entire bottom of the foot surface, shoe inserts that are removably placed between the foot and a shoe, shoe inserts that are attached to a shoe, and shoe inserts that are integrally built into a shoe.

Illustrative pillows as custom conformable devices according to the present invention are embodied by head pillows, neck pillows, back pillows, cushions that can be removably attached to various parts of the human body, and surgery pillows that are used to provide custom fit support during medical intervention into a patient's body, including anesthesia for surgical procedures.

Illustrative arm rests as custom conformable devices according to the present invention are embodied by cushions that provide custom fit support when in contact with any one of the various parts of a user's arm. Arm rests according to the present invention include embodiments for use with the arm merely resting on the arm rest, and embodiments for use with the arm rest removably attached to the arm, such as by strapping the arm rest to the arm.

Illustrative back rests as custom conformable devices according to the present invention are embodied by cushions that provide custom fit support to any one of various regions of a user's back when the cushion is placed between the user's back and a surface against which pressure is exerted. The cushion is detached from such surface in some of these embodiments, whereas the cushion is attached to such surface in other embodiments.

Illustrative orthopedic braces as custom conformable devices according to the present invention are embodied by cushions that are placed by a region of the anatomy of the user, such as a lower extremity region, and a brace framework, and by braces which have a cushion according to the present invention attached to or as an integral part of the brace.

Illustrative embodiments of devices such as shoe inserts, pillows, arm rests, and back rests according to the present invention comprise a portion with a cross-sectional view 100 as illustrated in FIG. 6. Expandable material 105 is comprised within bladder 102 that in the illustrative embodiment shown in FIG. 6 includes two layers 135 and 140. Layers 135 and 140 can be embodied together by a single layer in some embodiments of this invention.

The plurality of layers 135 and 140 in FIG. 6 illustrate an embodiment in which a containment layer 135 is surrounded by another layer 140. This multi-layering is preferred in embodiments in which various properties are optimized with various materials. For example, material layer 135 is in some embodiments chosen with superior gas impermeability properties, and material layer 140 is chosen with superior bio-compatibility, such as non-allergenic properties.

The portion of the cross-sectional view that is not shown in FIG. 6 comprises in some embodiments a portion of the custom conformable device that is provided with, for example, an additional valve. This additional valve is preferably mounted with respect to the bladder in a manner that is analogous to that shown for valve 110, and thus the full cross-sectional view of such multi-valve embodiment is not shown explicitly in the figures. As long as the valves in multi-valve embodiments perform according to the features and objectives of the present invention, the relative position and configuration of the various valves in such embodiments are not limitations of these type of embodiments of the custom conformable device of this invention. Accordingly, it is understood that the recitation of embodiments that comprise a valve or a means for controlling passage of gas into and from the bladder refers to embodiments that have only one valve and also to embodiments that have at least the explicitly recited valve.

The present invention envisages embodiments with bladders that have multi-layers comprising individual layers that are bonded to adjacent layers. Multi-layers that are contained within each other and they are not completely bonded to adjacent layers are also envisaged as part of the bladders in other embodiments of the present invention.

Embodiments of the present invention that comprise a multi-layered bladder satisfy, as the embodiments with a single-layer bladder do, the condition that the bladder is fluid-leak-proof at its attachment with valve 110. Furthermore, whether the bladder is single-layered or multi-layered, the bladder expands and contracts as fluid is admitted therein or expelled therefrom through valve 110, as expandable material in turn expands or contracts, respectively.

The location of valve 110 shown in FIG. 6 is illustrative, but not limiting. Valve 110 is located in other embodiments in other areas of bladder 102, preferably where it does not interfere with the support provided by the embodiment 100 of a custom conformable device according to the present invention.

Body 130 of illustrative embodiments of custom conformable devices such as shoe inserts, pillows, arm rests, and back rests according to the present invention is delineated by any one of a variety of perimeters 120 such as polygonal, arcuate, elliptical, circumferential, ovoidal, and combinations thereof. These various forms refer to the perimeters of any one of the possible cross-sections of body 130.

Illustrative embodiments of custom conformable devices such as shoe inserts, pillows, arm rests, and back rests according to the present invention expose an area 125 that comprises at least one of a variety of surfaces such as planar, curved, concave, convex, and combinations thereof. Area 125 is shown in FIG. 6 for illustrative purposes as being slightly convex at the top and the bottom of the cross-sectional view shown therein. This is an example, but not a limitation. The curvature of the top portion of area 125 is different from the curvature of the bottom portion of area 125 in other embodiments. Furthermore, the curvature of any one of top and bottom portions of area 125 is not constant in other embodiments. For example, certain regions of area 125 at the top and/or bottom are convex and other neighboring regions are concave.

Some illustrative embodiments of custom conformable devices such as shoe inserts, pillows, arm rests, and back rests according to the present invention comprise a body that is continuous throughout within its perimeter and exposed area. Other illustrative embodiments comprise a body that is discontinuous throughout its perimeter and exposed area, including embodiments with a body generally shaped like a geometric torus, embodiments with a multiply perforated body, and embodiments with at least two bodies attached to each other by a joint such as a seam, fastener, and clips.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A custom conformable device for providing self-adjustable arch support for a user's foot, the device comprising:
    an inflatable bladder configured to generally conform to fit under an arch of a foot,
    said inflatable bladder comprising an interior containing an open cellular foam material which substantially fills said interior, and
    a valve means for controlling passage of air into and from the open cellular foam material contained in the interior of the inflatable bladder,
        said valve means comprising an operable member which is normally closed so that when air is essentially completely expelled from the inflatable bladder the open cellular foam material is substantially compressed so as to create a partial vacuum within the bladder with the operable member in the normally closed position, and
        thereafter, with the inflatable bladder positioned under the arch of a user's foot while in a non-weight bearing position, said operable member is opened in response to activation by the user so that the inflatable bladder becomes self-inflating with the partial vacuum drawing air into the interior of the inflatable bladder and causing said open cellular material to expand and conform to the user's arch, and
        thereafter, as the operable member is permitted to return to the normally closed position, the open cellular material retaining a shape, during walking, that conforms to the user's arch as defined by the non-weight bearing position.

2. The device of claim 1, wherein the valve is a finger-activated valve.

3. The device of claim 2, wherein the finger-activated valve is a button valve.

4. The device of claim 1, wherein the valve is a central stem valve.

5. The device of claim 1, wherein the valve is a duck-bill valve.

6. The device of claim 1, wherein the valve is an umbrella valve.

7. The device of claim 1, wherein the open cellular foam material comprises medium-density polyurethane open cell foam.

8. The device of claim 1, wherein the open cellular foam material comprises at least one of open cell foamed polyester, open cell foamed polyether, and combinations thereof.

9. The device of claim 1, wherein the open cellular foam material comprises at least one of open cell glassy carbon foam, a combination of open cell foam and semi-closed foam, a combination of open cell foam and closed cell foam, a composite that includes open cell metal foam, and combinations thereof.

10. The device of claim 1, wherein the valve is a multiple activation valve.

11. The device of claim 1, wherein an insole of a shoe is attached to the self-inflating bladder.

12. The device of claim 1, wherein the bladder is attached to the interior of a shoe.

13. The device of claim 12, wherein the finger-activated valve extends through a portion of the shoe to the outside of the shoe for the multiple activation of the valve.

14. The device of claim 12, wherein the bladder is integrally built into the shoe.

15. The device of claim 1, wherein the open cellular material retains a shape that conforms to the user's arch as defined by the non-weight bearing position during movement of the foot.

16. The device of claim 1, wherein the inflatable bladder is positioned substantially exclusively under the arch.

17. The device of claim 1, wherein the open cellular material retains a shape that conforms to the user's arch as defined by the non-weight bearing position when a compressive force is provided by the foot.

18. The device of claim 1, wherein the open cellular material retains a shape that conforms to the user's arch as defined by the non-weight bearing position when weight is applied to the foot.

19. The device of claim 1, wherein the open cellular material retains a shape that conforms to the user's arch as defined by the non-weight bearing position regardless of a shifting weight applied on the foot.

20. The device of claim 1, wherein the inflatable bladder, prior to inflation, has a volume which is less than a space under the arch.

* * * * *